United States Patent [19]

Meyers et al.

[11] Patent Number: 4,967,021

[45] Date of Patent: Oct. 30, 1990

[54] PROCESS FOR PREPARATION OF DEUTERATED METHYLENE CHLORIDE

[75] Inventors: Cal Y. Meyers; Roch Chan-Yu-King, both of Carbondale, Ill.

[73] Assignee: Southern Illinois University Foundation, Carbondale, Ill.

[21] Appl. No.: 242,354

[22] Filed: Sep. 9, 1988

Related U.S. Application Data

[63] Continuation of Ser. No. 864,089, May 16, 1986, abandoned.

[51] Int. Cl.$^5$ .................. C07C 17/24; C07C 19/00; C07C 19/02
[52] U.S. Cl. .................................................. 570/101
[58] Field of Search ........................................ 570/101

[56] References Cited

U.S. PATENT DOCUMENTS

3,737,464   6/1973   Atkinson et al. .................. 570/101

FOREIGN PATENT DOCUMENTS

1085423   9/1980   Canada .................. 570/101

OTHER PUBLICATIONS

Dehmlow et al "Phase Transfer Catalysis" (1980), pp. 9, 10, 12 and 44.
Feldman et al, "J. Org. Chem.", vol. 50, No. 10, (1985), pp. 1746–1749.
Spillane et al, "J. Chem. Soc.", Perkin I, (1981), pp. 1763–1768.
Halpern et al, "J. Org. Chem.", vol. 48, No. 7, (1983), pp. 1022–1025.
Halpern et al, "Angew Chem.", Int. Ed. 23 (1984) No. 1, pp. 54 and 55.
Rabinonitz et al, "Angew Chem.", Int. Ed. Engl. 25 (1986), pp. 960–970.
Atkinson et al., "New Synthesis of Formaldehyde-$d_2$$^{1,2}$", Can. J. Chem., 47, (1969) pp., 477–479.

Primary Examiner—J. E. Evans
Attorney, Agent, or Firm—Senniger, Powers, Leavitt & Roedel

[57] ABSTRACT

A process for the preparation of deuterated methylene chloride. The process comprises contacting methylene chloride with an aqueous phase containing deuteroxide ions in the presence of a phase-transfer catalyst.

37 Claims, No Drawings

PROCESS FOR PREPARATION OF DEUTERATED METHYLENE CHLORIDE

This is a continuation of application Ser. No. 864,089, filed May 16, 1986 now abandoned.

BACKGROUND OF THE INVENTION

The present invention relates to the synthesis of deuterated methylene chloride, in general, and to the synthesis of deuterated methylene chloride under phase-transfer catalysis (P-T-C) conditions, in particular.

Dideuterio-methylene chloride (dichloromethane -$d_2$; $CD_2Cl_2$) has become increasingly important in industrial and research applications as a reagent for chemical reactions, as a solvent for inorganic and organic compounds in various NMR spectroscopy, and in other applications where the properties of methylene chloride are desirable but where its protons must be replaced by deuterium. In particular, $CD_2Cl_2$ is being recommended for applications where $CDCl_3$ or even $CH_2Cl_2$ were formerly used. For example, because many inorganic compounds and complexes are more soluble in $CD_2Cl_2$ than in $CDCl_3$, it has been recommended that $CD_2Cl_2$ be used as a solvent in place of $CDCl_3$ in NMR spectroscopy. In addition, reports have indicated that $CD_2Cl_2$ is less toxic to mammals than is $CH_2Cl_2$ and for that reason it may be preferable to use $CD_2Cl_2$ in certain applications.

Although $CD_2Cl_2$ offers many advantages over other reagents, at the present there is not a method of preparation that provides high yields of a highly deuterated methylene chloride at a low cost. For instance, Atkinson et al. in *Chem. Abstr.* 1970, 72, 110766y disclose a method of deuteration of $CH_2Cl_2$ to $CD_2Cl_2$ that is carried out in a homogeneous solution; $CH_2Cl_2$ in dimethyl sulfoxide is mixed with $D_2O$ containing NaOD and refluxed 24 hours to provide methylene chloride containing 33% D. It was reported that this product could be further enriched to 42% D by repeating the process (recycling). In the absence of dimethyl sulfoxide, no exchange occurs.

In many applications, however, it is preferable to use methylene chloride having a content in excess of 99% D. To achieve such a high percent of D/H substitution by using the method of Atkinson et al. would require a number of enriching cycles at 24 hours of refluxing per cycle. Because of the number of recycles required in order to obtain methylene chloride having a D content in excess of 99%, the productivity of the process would be poor. Moreover, because methylene chloride is soluble in dimethyl sulfoxide, it is not feasible to remove the deuterated product ($CD_2Cl_2$) by simple layer separation. Furthermore, their exchange fails in the absence of dimethyl sulfoxide. As a consequence, the cost of preparing $CD_2Cl_2$ by the Atkinson et al. process would be relatively high.

Other methods for preparing deuterated methylene chloride have been reported in the chemical literature. Myers et al. (*J. Chem. Phys.* 1952, 20, 1420–1427) and Shimanouchi et al. (*J. Mol. Spectrosc.* 1962, 8, 222–235) describe the preparation of deuterated methylene chloride by heating chloroform-d ($CDCl_3$) with metallic zinc in $CH_3CO_2D$. Leitch et al (*Can. J. Chem.* 1953, 351–356) describe treating $CD_2O$ with $PCl_5$ to yield $CD_2Cl_2$. In the former method, the yield is poor and much of the costly $CDCl_3$ and $CH_3CO_2D$ are destroyed in the process. In the latter method, the required starting material ($CD_2O$) is very costly and difficult to prepare in anything other than small laboratory amounts.

Accordingly, a need has remained for an improved simple and economic method for preparing and isolating deuterated methylene chloride on a large scale.

SUMMARY OF THE INVENTION

The present invention is thus directed to a method for preparing deuterated methylene chloride; a method of preparation which provides the deuterated methylene chloride in high yields; and a method of preparation which minimizes the cost of raw materials and which does not require an excessive number of recycles to obtain dideuterated methylene chloride having a D content in excess of 99%.

Briefly, therefore, the present invention is directed to a process for the preparation of deuterated methylene chloride. The process comprises contacting methylene chloride with an aqueous phase containing deuteroxide ions in the presence of a phase-transfer catalyst.

Other objects and features will be in part apparent and in part pointed out hereinafter.

DESCRIPTION OF THE PREFERRED EMBODIMENT

In accordance with the present invention, it has surprisingly been found that deuterium may be essentially quantitatively exchanged for the hydrogens of methylene chloride under phase-transfer conditions, without the need of cosolvents, and without decomposition of the product. In this process, methylene chloride is contacted with an aqueous phase that is basic in nature and comprises deuteroxide ions (OD$^-$) Preferably, the aqueous phase is a concentrated base and in a most preferred embodiment the aqueous phase comprises a saturated or supersaturated solution of base in an aqueous medium. Thus, for example, the aqueous phase may comprise a deuteroxide base dissolved in water, a base dissolved in $D_2O$ or a metal oxide mixed with $D_2O$.

Regardless of the manner in which the aqueous phase is prepared, however, it is preferred that the relative amount of deuterium atoms to hydrogen atoms be as high as possible. Thus, it is particularly preferred that the aqueous phase be prepared by dissolving a deuteroxide base such as NaOD in $D_2O$ or by dissolving an alkali metal oxide such as sodium oxide ($Na_2O$) in $D_2O$. Most preferably, the aqueous phase is prepared by dissolving sufficient sodium oxide in $D_2O$ in the molar ratio of about 1 to 5, respectively.

Certain tetraalkylammonium salts have been found to have an especially advantageous effect in promoting the exchange of deuterium for hydrogen of methylene chloride including methyltricaprylylammonium chloride and tetrabutyl-ammonium (TBA) chloride, bromide and hydrogen sulfate. The most preferred phase transfer catalyst is TBA hydrogen sulfate. Various other quaternary ammonium and phosphonium salts and cationic surfactants may be used in accordance with the present invention, and a substantial number of these may be expected to provide reasonable conversions per cycle. However, it must be recognized that changes in the alkyl substituents as well as of the anion of the salts can significantly affect the efficiency of the reaction To achieve deuteration of the methylene chloride under base-catalyzed phase-transfer conditions, it is necessary that the phase-transfer agent be present in a catalytic amount. Although the amount of catalyst will vary according to the desired rate of reaction and the particular catalyst selected, it is generally preferred that the amount of the catalyst be in the range of about 0.1 to about 20 mole percent of the methylene chloride. For the methyltricaprylylammonium chloride and TBA salts, it is particularly preferred to use a molar ratio of catalyst to methylene chloride somewhere in the range of about 0.004 (0.4 mole percent) Higher concentrations of catalyst may be used with a corresponding increase in the rate of reaction. Similarly, lesser concentrations of catalyst may be used with a corresponding decrease in the rate of reaction The relative proportions of aqueous phase and methylene chloride may be varied and the ratio of the two is not considered to be narrowly critical. Where the aqueous phase comprises a solution of NaOD in $D_2O$ as described above, it is preferred that the methylene chloride/sodium deuteroxide/$D_2O$ have a molar ratio of about 1½, respectively.

In a preferred embodiment, the D/H substitution of methylene chloride is thus achieved by its reaction with the aqueous base and $D_2O$ in the presence of a catalytic amount of a phase-transfer agent. As the reaction proceeds, the DOD and OD$^-$ content of the aqueous phase is progressively depleted as the $CD_2Cl_2$ content of the organic phase is increased Ultimately, an overall equilibrium is reached at which the hydrogen/deuterium ratio within the methylene chloride is constant, wherein this equilibrium ratio is controlled by the total number of hydrogen and deuterium atoms which are available for exchange. A theoretical equilibrium maximum of D/H exchange for a particular reaction, therefore, can be calculated by determining the percent of exchangeable deuterium atoms in the total of exchangeable deuterium plus hydrogen atoms in the reaction mixture.

Accordingly, methylene chloride with a desired degree of D/H substitution can be prepared in two different manners. First, it can be prepared through a selection of system parameters which will provide a theoretical maximum of D/H exchange in a single reaction that is at least equal to the desired degree of substitution. Alternatively and preferably, the desired degree of D/H substitution may be achieved through one or more recycles of the methylene chloride through the reaction scheme. Thus, after a first reaction of the methylene chloride with an aqueous phase containing a source of deuterium, the partially deuterated methylene chloride is separated from the first aqueous phase and then treated with a second (fresh) aqueous phase and catalyst. This sequence can be repeated to achieve the desired percent of D in the methylene chloride.

After recovery of the $CD_2Cl_2$ product, the residual aqueous phase(s) contain substantial amounts of deuterium in the form of $D_2O$, DOH and NaOD. Distillation of the aqueous phase, therefore, affords $D_2O$, DOH and $H_2O$ from which the $D_2O$ can be recovered and used again in this deuteration procedure to prepare deuterated methylene chloride. The recovery and reuse of the $D_2O$ substantially contributes to the economy of this process.

Furthermore, the process of the present invention offers the additional advantage of ease of recovery of the product $CD_2Cl_2$. Conveniently, the $CD_2Cl_2$ product can be recovered by decanting the reaction mixture or through the use of distillation.

The following examples illustrate the invention.

EXAMPLE 1

D/H Exchange of $CH_2Cl_2$ With $D_2O$-NaOH under P-T-C Conditions (Aliquat 336)

(a) Control Reaction With $H_2O$, 3 hours

A solution composed of $CH_2Cl_2$ (1 mL; 0.016 mol) and methyltricaprylylammonium chloride (Aldrich Chemical Co., Milwaukee, WI, sold under the trademark of Aliquat 336) (0.031 g; 0.0001 mol) was added to a 50% w/w (weight percent) aqueous solution of NaOH (1 mL; 0.019 mol). This mixture was stirred under argon at room temperature for 3 h and then diluted with $CCl_4$ (4 mL) and $H_2O$ (1 mL). The organic layer was separated, dried (MgSO$_4$), and submitted to $^1$H NMR and IR studies.

$^1$H NMR (CCl$_4$): 65.29 (s, area 5.60, CH$_2$ of CH$_2$Cl$_2$).

IR (CCl$_4$ solution, double beam with CCl$_4$ in the reference cell): 3055 (CH$_2$ asym str.), 2990 (CH$_2$ sym str.), 2935, 2860, 2691, 2406, 2304, 1424 (CH$_2$ scis.), 1381 (w), 1262 (CH$_2$ wag.), 1157 (CH$_2$ twist.), 1140 (s), 897 (CH$_2$ rock ), 739 (s), 706 (s), 641 (w), 621 cm$^{-1}$.

(b) Reaction With $D_2O$, hours

To 1 mL of a 50% w/w solution of NaOH (0.019 mol) in $D_2O$ (99.7% D, Wilmad Glass Co., Inc., Buena, NJ) was added a solution composed of 1 mL (0.016 mol) of CH$_2$Cl$_2$ and 0.031 g (0.0001 mol) of Aliquat 336. This mixture was stirred for 3 h, then diluted with 4 mL of CCl$_4$ and 1 mL of $D_2O$. The isolated organic layer was dried (MgSO$_4$) and submitted to $^1$H NMR and IR studies. $^1$H NMR (CCl$_4$): 6 5.29 [br s (split at about half height), area 4.50, CH of CHDCl$_2$ and CH$_2$ of CH$_2$Cl$_2$]; thus, the CH$_2$Cl$_2$ underwent 19.6% D/H exchange. [% D/H exchange=100-[integration area (CH$_2$Cl$_2$+CHDCl$_2$) from reaction with $D_2O$÷integration area (CH$_2$Cl$_2$) from control reaction with $H_2O$] X 100. For this determination, a portion of the CCl$_4$ solution was transferred to an NMR tube to a specific height and the $^1$H NMR integration area was compared to that of the CCl$_4$ solution from the control reaction (CH$_2$Cl$_2$-$H_2O$) worked up and placed in an NMR tube in the identical manner.] Since the maximum calculated exchange at equilibrium is 60% under these conditions, the observed exchange represents 33% of the theoretical maximum. The presence of CHDCl$_2$ and CD$_2$Cl$_2$ in the crude mixture was confirmed by IR spectroscopy.

IR (CCl$_4$ solution, double beam with CCl$_4$ in the reference cell): 3055 (CH$_2$ asym str. of CH$_2$Cl$_2$), 3019 (CH str. of CHDCl$_2$), 2985 (CH$_2$ sym str. of CH$_2$Cl$_2$), 2960, 2932, 2304 (CD$_2$ asym str.), 2250 (CD str. of CDHCl$_2$), 2205 (CD$_2$ sym str.), 1424 (CH$_2$ scis.), 1408, 1262 (CH wag. of CH$_2$Cl$_2$), 1218 (CH bend. of CHDCl$_2$), 1141, 1085, 1021, 957 (CD$_2$ wag. of CD$_2$Dl$_2$, 885 (CD bend. of CHDCl$_2$), 739, 695 (s), 641 (w), 615 cm$^{-1}$.

The observed CHD and CDD vibrations of CHDCl$_2$ and CD$_2$Cl$_2$ are identical to those reported by T. Shimanouchi and I. Suzuki (*J. Mol. Spectrosc.* 1962, 8, 222–235).

(c) Control Reaction with $H_2O$, 28.5 hours

The procedures of part (a) above were repeated except that the period for reaction was 28.5 h. The $^1$H NMR spectrum exhibited an integration of 4.10 for Cl$_2$CH$_2$ (δ 5.29).

(d) Reaction With D$_2$O, 28.5 hours

The procedures of part (b) above were repeated except that the period for reaction was 28.5 h. Integration of the $^1$H NMR signals at $\delta$5.29 (Cl$_2$CH$_2$ and Cl$_2$CHD) was 1.81; which (based on the standard area of 4.10 determined with the same instrument setting) indicated that there was 55.8% D/H exchange when calculated as set out in part (b) above (93% of the theoretical maximum).

The IR spectrum was qualitatively similar to that obtained in (b), but the vibrations associated with the D-C-D group became far more prominent.

EXAMPLE 2

Treatment of CH$_2$Cl$_2$ With D$_2$O-NaOH in the Absence of Phase-Transfer Catalyst The experiments with D$_2$O described in Example 1 were carried out in the absence of phase-transfer catalyst for 24.5 h and 28.5 h, respectively. Unlike the results of the D$_2$O experiments of Examples 1 (b) and (d), the IR spectra of the organic layers were identical to that of CH$_2$Cl$_2$; no C-D vibrations were exhibited. No D/H exchange occurred.

EXAMPLE 3

D/H Exchange of CH$_2$Cl$_2$ With D$_2$O-Na$_2$O Under P-T-C Conditions (Aliquat 336)

(a) In The Presence of Air (atmospheric O$_2$; absence of moisture)

A 3-necked flask immersed in an ice-water bath and connected via stopcock (closed) to an argon-filled balloon, was charged with 5.00 g (0.25 mol) of D$_2$O (99.7% D, Wilmad Glass Co.), followed by the addition of 3.10 g (0.049 mol) of Na$_2$O (Alfa Products/Morton Thiokol, Inc., Danvers, MA), in small portions. Because Na$_2$O reacts violently with water, the addition was carried out slowly and evenly with constant stirring. The argon-filled balloon connector was then opened and the reaction vessel was purged with argon by venting through a loosely stoppered neck. The stopper was then replaced tightly but the connector to the argon-filled balloon was kept open. It should be noted that the air (O$_2$ but not moisture) quite rapidly diffuses through the thin rubber of an argon-filled balloon; in 14 hours the reaction would have been subjected to many volumes of dry air. The ice-water bath was then removed. To this stirred mixture was injected (through a rubber septum) a solution composed of 8.50 g (0.10 mol) of CH$_2$Cl$_2$ and 0.17 g (0.0004 mol) of Aliquat 336. The resulting mixture was stirred for 14 h after which time an aliquot of the organic layer (upper layer) was taken for direct $^1$H NMR analysis. % D/H exchange=100−[(integration area observed (CH$_2$Cl$_2$+CHDCl$_2$)÷integration area of external pure CH$_2$Cl$_2$)]X 100.

$^1$H NMR (neat): $\delta$5.32 [s, peak split at half height, integration area 3.20, CHDCl$_2$ and CH$_2$Cl$_2$]. ACS-grade CH$_2$Cl$_2$ external $^1$H NMR standard: integration area 5.80 ($\delta$5.32). From these data it was calculated that 45% D/H exchange had occurred in the 14-h period, or 63% of the maximum attainable % D at equilibrium (under these conditions, the maximum (equilibrium) D/H exchange is 71%).

(b) In The Absence of Air (atmospheric O$_2$ and moisture)

Reaction (a) was repeated but after the argon purge of the reaction vessel the stopcock to the argon-filled balloon was closed before the CH$_2$Cl$_2$-Aliquat 336 solution was injected through the rubber septum. The reaction mixture was thus sealed from the ambience during the 14-h reaction period.

$^1$H NMR (neat) analysis (see (a) above) after the 14-h reaction indicated that 44% D/H exchange had occurred (63% of that possible at equilibrium).

A comparison of (a) and (b) shows that the presence of air (O$_2$, absence of moisture) seems to have little effect on the rate of this D/H exchange reaction.

EXAMPLE 4

Kinetic Studies of D/H Exchange of CH$_2$Cl$_2$ With D$_2$O-Na$_2$O Under P-T-C Conditions. (Aliquat 336)

In a three-necked, round-bottomed flask (cooled in an ice-water bath) was placed 5.00 g (0.25 mol) of D$_2$O (99.9% D, Norell, Inc., Landisville, NJ), followed by the careful addition of 3.10 g (0.049 mol) of Na$_2$O in small portions while the solution was being stirred.

The ice bath was then removed and a solution composed of 8.50 g (0.1000 mol) of CH$_2$Cl$_2$ and 0.17 g (0.0004 mol) of Aliquat 336 was added. Aliquots of the organic layer were taken for direct $^1$H NMR analysis after reaction periods of 20 h, 44 h, 74 h and 119 h and the percentages of D/H exchange were determined as described in Example 3 (a). The maximum possible % D/H exchange (calculated for equilibrium) is 71.00%. The observed % D/H exchange (with percent relative to maximum possible in parentheses) are as follows: 20 h, 62.35% (87%); 44 h, 66.13% (93%); 74 h, 70.86% (100%); 119 h, 73.13% (100%).

EXAMPLE 5

The Enhancement of Incorporation of Deuterium into CH$_2$Cl$_2$ by the use of Sequential Recycling Run A Into a 500-mL round-bottomed flask cooled in an ice-water bath was added 16.70 g (0.84 mol) of D$_2$O (99.7% D) followed by 10.33 g (0.16 mol) of Na$_2$O in small portions with stirring. Although this run was carried out under argon, this precaution is not required.

The ice-water bath was then removed and a solution composed of 29.00 g (0.34 mol) of CH$_2$Cl$_2$ and 0.55 g (0.0014 mol) of Aliquat 336 was added. After the reaction proceeded for 30 h, an aliquot of the organic layer was removed for $^1$H NMR analysis; 71.22% D/H exchange had occurred, which is 100% of the calculated equilibrium maximum.

First Recycle

The above crude mixture was cooled with an ice-water bath and the organic layer (upper layer) was separated via pipette from the aqueous layer. The isolated organic layer was then treated with fresh D$_2$O, Na$_2$O and catalyst in the same proportions and manner as stated above for the methylene chloride. $^1$H NMR analysis of an aliquot taken from the organic layer after 41 h of reaction indicated a total of 93.12% D/H exchange had occurred, which is 100% of the calculated equilibrium maximum.

Second and Third Recycles

The second and third recycles, respectively, were performed as described above for the first recycle. $^1$H NMR analysis of an aliquot removed from the organic layer after 30 h and 34 h of reaction for the second and third recycles, respectively, indicated that a total of 98.65% and 99.12% D/H exchange had occurred, both of which represent 100% of the calculated equilibrium maximum, respectively. The methylene chloride, isolated after the third recycle by distillation, b.P. 38.8° C. [azeotrope: methylene chloride-1% water ("Handbook of Chemistry and Physics", 51 Edition, Chemical Rubber Co., Cleveland, page D-31)], was shown by $^1$H NMR to have incorporated 98.77% D.

Run B

Into a 500-mL glass-jacketed flask was placed 16.70 g (0.84 mol) of $D_2O$ (99.9% D, Norell Inc.); cold water (5° C.) was allowed to flow through the glass jacket. To this cold $D_2O$, 10.33 g (0.16 mol) of $Na_2O$ was slowly added in small portions while the solution was stirred. The cold water in the jacket was then replaced with water 24° C. and a solution composed of 29.00 g (0.34 mol) of $CH_2Cl_2$ and 0.55 g (0.0014 mol) of Aliquat 336 was added to the reaction solution. Stirring was continued for 15.5 h after which time an aliquot was removed from the organic layer and analyzed by $^1$H NMR, which indicated that the methylene chloride had undergone 42.4% D/H exchange. The contents of the NMR tube were poured back into the reaction flask and stirring was continued for an additional 10 h; $^1$H NMR analysis of the organic phase indicated that the methylene chloride had undergone 61.2% D/H exchange (86% of equilibrium maximum). The reaction mixture was then distilled (hot water at 50°-60° C. flowing into the glass jacket) and 25.60 g of the deuterated methylene chloride (b.p. 38.8° C., azeotrope: methylene chloride-1% water) was collected.

First Recycle

In the same manner as described immediately above, 16.70 g (0.84 mol) of $D_2O$ (99.9% D) was placed in a cold-water jacketed flask followed by the addition of 10.33 g (0.16 mol) of $Na_2O$ in small portions. Water at 24° C. was then allowed to flow through the jacket and a solution of partially deuterated methylene chloride (25.60g), collected as described above, and 0.55 g (0.0014 mol) of Aliquat 336, was added to the mixture. $^1$H NMR indicated that after 24 h of reaction the methylene chloride contained 83.00% D (91% of equilibrium maximum).

The crude mixture was then distilled (hot water at 50°-60 ° C. flowing in the jacket), and 21.50 9 of the deuterated methylene chloride (b.p. 38.8° C., azeotrope containing 1% water) was collected.

Second and Third Recycles

The partially deuterated methylene chloride (21.50g) collected by distillation, above, was treated again with $D_2O$, $Na_2O$, and Aliquat 336 as described above for the first recycle. $^1$H NMR analysis of the organic layer after 21 h of reaction indicated that the methylene chloride now contained 94.2% D (97% of the equilibrium maximum). Continued stirring for an additional 11 h raised the value to 95.9% D (98% of the equilibrium maximum). Distillation of the organic layer afforded 18.70 g of this deuterated methylene chloride.

The D/H exchange procedure was repeated again (third recycle) with the 18.70 g of distillate for a period of 55 h and the product, collected by distillations b.p 38.8° C., 15.37 g, was shown by $^1$H NMR analysis to contain 98.57% D (99.6% of the equilibrium maximum).

$^1$H NMR (neat distillate): δ5.32 (s, barely detectable, $CHDCl_2$).

IR (neat distillate): 3350 (w), 3135 (w), 3020 (vw, CH str. of $CHDCl_2$), 2962 (w), 2305 (s, $CD_2$ asym str. of $CD_2Cl_2$), 2205 (s, $CD_2$ sym str. of $CD_2Cl_2$), 2100 (w), 1390 (w), 1250 (w), 1135 (br, 998 (w), 955 (s, $CD_2$ wag. of $CD_2Cl_2$), 888 (w, CD bend. of $CD_2Cl_2$), 865 (w), 715 (s), 680 (w), 635 (w) cm$^{-1}$.

The results from runs A and B of Example 5 are summarized below in Table I.

TABLE I

The Effect of Recycling On the Extent of D/H Exchange of Methylene Chloride with $D_2O/Na_2O$/Aliquat 336.

| | % D IN METHYLENE CHLORIDE | | |
|---|---|---|---|
| | Calculated Maxmium at Equilibrium[b] | Determined[a] Run A | Run B |
| Initial exchange | 71.00 | 71.22 (30h) | 61.20 (25.5h) |
| First recycle | 91.60 | 93.12 (41h) | 83.00 (24h) |
| Second recycle | 97.50 | 98.65 (30h) | 95.90 (32h) |
| Third recycle | 99.01 | 99.12 (34h) 98.77[c] | 98.57[c] (55h) |

[a]Values determined on undistilled product except where indicated otherwise.
[b]The maximum theoretical (equilibrium) extent of D/H exchange after each recycle procedure was calculated a priori, i.e., not from the determined % D of that methylene chloride, but from the calculated % D, although the results would not differ significantly.
[c]% D of distilled (isolated) product.

EXAMPLE 6

D/H Exchange of $CH_2Cl_2$ With $D_2O$-$Na_2O$ Catalyzed by Aliquat 336. Determination of relative rate of Exchange and Extent of Decomposition of Methylene Chloride.

A 1-L round-bottomed flask equipped with a condenser (water cooled, 10° C.) fitted with a calcium chloride drying tube was charged with 16.70 g (0.84 mol) of $D_2O$ (99.7% D., Wilmad Glass Co.) and stirring was begun while the flask was immersed in an ice water bath. In small portions 10.33 g (0.17 mol) of $Na_2O$ was added followed by a solution composed of 29.00 g (0.34 mol) of $CH_2Cl_2$ and 0.55 g (0.0014 mol) of Aliquat 336. The resulting mixture was stirred at 10°-15° C. and aliquots of the organic layer were taken after 1, 2, 3, 5, and 6 h of reaction, respectively, and analyzed directly by $^1$H NMR. The results are summarized in Table II below.

The residual reaction mixture was kept overnight in the freezer and 11.70 g of organic material (upper layer) was isolated via pipette from the frozen lower aqueous layer and distilled to provide 4.90 g of partially deuterated methylene chloride. The aqueous layer, 25.10 g, was allowed to melt and 2.55 g was removed, acidified with 1N $HNO_3$ (until pH ca. 1), and treated with 5% aqueous $AgNO_3$ solution. The precipitated AgCl was collected, washed thoroughly with distilled water followed by acetone, and dried in an oven (90° C., 20 min) to afford 0.07 g (0.0005 mol) of AgCl, which extrapolates to 0.70 g (0.005 mol) of AgCl calculated based on the total aqueous layer. Taking into account the 0.0014 mol of Cl$^-$ emanating from the Aliquat 336 used, no more than 0.0036 mol of Cl$^-$ came from the methylene chloride; i.e. no more than 1% of the methylene chloride underwent decomposition or reaction other than D/H exchange during its 6-h contact with 50% alkali under these P-T-C conditions. This result indicates that dichloromethyl anion ($Cl_2CH^-$), in contrast to trichloromethyl anion ($Cl_3C^-$), undergoes $\gamma$-elimination substantially more slowly than protonation/deuteration, and that methylene chloride undergoes negligible $S_N2$ displacement of $Cl^-$ by $^-OH$ ($^-OD$) even under these phase-transfer conditions. In summary, methylene chloride undergoes D/H exchange under these conditions essentially without any decomposition, in surprising contrast to chloroform.

TABLE II

Relative Rate of D/H Exchange of $CH_2Cl_2$ with $D_2O/Na_2O$/Aliquat 336

| Reaction Time, h at 10° C. | D/H Exchange % observed | % of equilibrium maximum[a] |
|---|---|---|
| 1 | 27.58 | 38.8 |
| 2 | 33.89 | 47.7 |
| 3 | 48.14 | 67.8 |
| 5 | 53.85 | 75.8 |
| 6 | 57.69 | 81.3 |

[a]equilibrium maximum is 71% for these condition.

EXAMPLE 7

D/H Exchange of $CH_2Cl_2$ with $D_2O$-$Na_2O$ phase transfer catalyzed with Tetrabutylammonium Hydrogen Sulfate (TBA Hydrogen Sulfate)

To a round-bottomed flask, immersed in an ice-water bath and equipped with a cold-water condenser fitted with a $CaCl_2$-drying tube, was added 5.00 g (0.25 mol) of $D_2O$ followed by 3.10 g (0.049 mol) of $Na_2O$ added in small portions while the mixture was stirred.

The ice-water bath was then removed, and to the stirred mixture was added a solution composed at 8.50 g (0.10 mol) of $CH_2Cl_2$ and 0.136 g (0.0004 mol) of tetrabutylammonium hydrogen sulfate (Sigma Chemical Co., St. Louis, MO). Aliquots of the organic layer (upper layer) taken for $^1H$ NMR analysis provided the following results: 3 h, 63.04% D/H exchange (89% of maximum equilibrium value); 4 h, 65.30% D/H exchange (92% of maximum equilibrium value). The calculated D/H exchange at equilibrium is 71.0%.

These data show that the rate of D/H exchange is much faster catalyzed with tetrabutylammonium hydrogen sulfate compared with Aliquat 336. The difference would have been very much larger had the sample been compared earlier in the exchange well before equilibrium was approached in the TBA hydrogen sulfate-catalyzed reaction.

EXAMPLE 8

D/H Exchange of $CH_2Cl_2$ with $D_2O$-$Na_2O$ Phase-Transfer catalyzed with Tetrabutylammonium chloride (TBA Chloride)

In a manner like that described in Example 7, D/H exchange of $CH_2Cl_2$ was carried out in the presence of tetrabutylammonium chloride (Aldrich Chem. Co.) [0.111 g (0.0004 mol)] instead of TBA hydrogen sulfate. $^1H$ NMR analysis of an aliquot of the organic layer (upper layer) after 3 h of reaction indicated that 44.7% D/H exchange had occurred (63% of the maximum equilibrium amount.)

EXAMPLE 9

D/H Exchange of $CH_2Cl_2$ with $D_2O$-$Na_2O$ Phase-Transfer catalyzed with Tetrabutylammonium Bromide (TBA Bromide)

In a manner like that described in Example 7, D/H exchange of $CH_2Cl_2$ was carried out in the presence of tetrabutylammonium bromide (Aldrich Chem. Co.) [0.129 g (0.0004 mol)] instead of TBA hydrogen sulfate. $^1H$ NMR analysis of an aliquot of the organic layer (upper layer) after 3 h of reaction indicated that only 1.1% D/H exchange had occurred (1.5% of the maximum equilibrium amount). Because of this unexpectedly poor yield of D/H exchange, the attempt was repeated with fresh materials. The results were similar: only 2.3% D/H exchange had occurred over the 3-h period (3.2% of the maximum equilibrium amount).

Examples, 7, 8, and 9 all describe the use of a tetrabutylammonium salt as the phase-transfer catalyst in these D/H exchanges of $CH_2Cl_2$. A comparison of the results illustrate the unexpected importance of the role of the counteranion of the quaternary ammonium catalyst. Thus, the hydrogen sulfate catalyst is of the order of several powers of 10 times more effective than the bromide, while the chloride is intermediary in activity. Surprising also, from the one comparison available in this series, is the observation that the structure of the alkyl groups of the quaternary ammonium catalyst appears to have but little influence on the rate of this exchange, viz., $CH_3N^+((CH_2)_7CH_3)_3Cl^-$ (Aliquat 336) and $(CH_3CH_2CH_2CH_2)_4N^+Cl^-$ (TBA chloride) under almost identical conditions induce D/H exchange at about the same rates—a result quite unexpected in light of literature reports (e.g., W.J. Spillane, P. Kavanagh, F. Young, H.J.M. Dou, and *J. Metzger, J. Chem. Soc., Perkin Trans.* 1 1981, 1763–1768).

These results are compared in Table III.

TABLE III

Efficiency of D/H Exchange of $CH_2Cl_2$ in 50% $NaOD/D_2O$ Catalyzed by $(\underline{n}\text{-Bu})_4N^+X^-$ (at 25° C.).[a] Influence of $X^-$ and Comparison with $CH_3N^+((CH_2)_7CH_3)_3Cl^-$

| P-T Catalyst $(\underline{n}\text{-Bu})_4N^+X^-$ where X is | D/H Exchange[b] in 3 h Actual, % | of Theoretical, % |
|---|---|---|
| $HSO_4$ | 63 (63)[c] | 89 (92)[c] |
| Cl | 45 | 63 |
| Br | 1.7 ± 0.6[d] | 2.4 ± 0.8[d] |
| $CH_3N^+((CH_2)_7CH_3)_3Cl^-$ (Aliquat 336)[e] | 48 | 68 |

[a]$CH_2Cl_2$, 0.10 mol; (n-Bu)$_4$N$^+$X$^-$, 0.004 mol; Na$_2$O, 0.049 mol; D$_2$O, 0.25 mol (i.e., 50% w/w NaOD/D$_2$O).
[b]Theoretical maxium (Equilibrium) D/H exchange under these conditions is 71%.
[c]In 4 h.
[d]Based on two runs.
[e]Included for comparison; mole ratio of all materials is the same as that noted in footnote (a); data from Example 6.

In view of the above, it will be seen that the several objects of the invention are achieved and other advantageous results are attained.

As various changes could be made in the above methods and products, without departing from the scope of the invention, it is intended that all matter contained in the above description shall be interpreted as illustrative and not in a limiting sense.

What is claimed is:

1. A process for the preparation of deuterated methylene chloride comprising contacting methylene chloride with an aqueous phase containing deuterium oxide and a base in the presence of a phase-transfer catalyst.

2. A process as set forth in claim 1 wherein the phase-transfer catalyst comprises a cationic surfactant.

3. A process as set forth in claim 1 wherein the phase-transfer catalyst comprises a tetraalkylammonium salt.

4. A process as set forth in claim 1 wherein the phase transfer catalyst comprises methyltricaprylammomonium chloride.

5. A process as set forth in claim 1 wherein the phase transfer catalyst comprises a tetrabutylammonium salt.

6. A process as set forth in claim 1 wherein the phase transfer catalyst comprises tetrabutylammonium hydrogen sulfate.

7. A process as set forth in claim 1 wherein the aqueous phase is prepared by the addition of a base to $D_2O$.

8. A process as set forth in claim 1 wherein the aqueous phase is prepared by the addition of a deuteroxide base to $D_2O$.

9. A process as set forth in claim 1 wherein the aqueous phase is prepared by the addition of NaOD to $D_2O$.

10. A process as set forth in claim 1 wherein the aqueous phase is prepared by dissolving a deuteroxide base in $H_2O$.

11. A process as set forth in claim 1 wherein the aqueous phase comprises a saturated solution of a base in $D_2O$.

12. A process as set forth in claim 1 wherein the aqueous phase comprises a supersaturated solution of a base in $D_2O$.

13. A process as set forth in claim 1 wherein the aqueous phase is prepared by dissolving a metallic oxide in $D_2O$.

14. A process as set forth in claim 9 wherein the aqueous phase is prepared by dissolving sodium oxide in $D_2O$.

15. A process as set forth in claim 9 wherein the aqueous phase is prepared by dissolving sodium oxide in $D_2O$ in the molar ratio of about 1 to 5, respectively.

16. A process as set forth in claim 1 wherein the mole percent of the phase-transfer catalyst based on the methylene chloride content is at least about 0.1%.

17. A process as set forth in claim 1 wherein the mole percent of the phase-transfer catalyst based on the methylene chloride content is in the range of about 0.1% to about 20%.

18. A process as set forth in claim 1 wherein the mole percent of the phase-transfer catalyst based on the methylene chloride content is about 0.4%.

19. A process as set forth in claim 1 wherein the molar ratio of methylene chloride to deuteroxide ions to $D_2O$ is about 1½, respectively.

20. A process as set forth in claim 1 further comprising separating the methylene chloride from the aqueous phase after the two are contacted in the presence of a phase transfer catalyst.

21. A process as set forth in claim 20 wherein the methylene chloride is separated by decanting the methylene chloride from the aqueous phase.

22. A process as set forth in claim 21 further comprising freezing the aqueous phase prior to the step of decanting and thereafter decanting the methylene chloride from the frozen aqueous phase.

23. A process as set forth in claim 20 wherein the methylene chloride is separated from the aqueous phase by distillation.

24. A process as set forth in claim 23 wherein the distilled product is dried over a drying agent.

25. A process as set forth in claim 20 further comprising one or more recycling steps which comprise contacting the separated methylene chloride with a fresh aqueous phase containing deuterium oxide and a base in the presence of a phase-transfer catalyst, and separating the methylene chloride from the aqueous phase.

26. A process for the preparation of deuterated methylene chloride comprising
dissolving $Na_2O$ in $D_2O$ to form an aqueous phase, and
contacting methylene chloride with the aqueous phase in the presence of a catalytic amount of a phase transfer catalyst.

27. A process as set forth in claim 26 wherein the phase-transfer catalyst comprises a cationic surfactant.

28. A process as set forth in claim 26 wherein the phase-transfer catalyst comprises a tetraalkylammonium salt.

29. A process as set forth in claim 26 wherein the phase-transfer catalyst comprises methyltricaprylylammomonium chloride.

30. A process as set forth in claim 26 wherein the phase-transfer catalyst comprises a tetrabutylammonium salt.

31. A process as set forth in claim 30 wherein the tetrabutylammonium salt is selected from the group consisting of tetrabutylammonium hydrogen sulfate, tetra-butylammonium chloride and tetrabutylammonium bromide.

32. A process as set forth in claim 26 wherein the mole percent of the phase-transfer catalyst based on the methylene chloride content is at least about 0.1%.

33. A process as set forth in claim 26 wherein the aqueous phase comprises a supersaturated solution of $Na_2O$ in $D_2O$.

34. A process as set forth in claim 26 wherein the aqueous phase comprises a saturated solution of $Na_2O$ in $D_2O$.

35. A process as set forth in claim 26 wherein the aqueous phase is prepared by dissolving sodium oxide in $D_2O$ in the molar ratio of about 1 to 5, respectively.

36. A process as set forth in claim 26 wherein the molar ratio of methylene chloride to deuteroxide ions to $D_2O$ is about 1½, respectively.

37. A process as set forth in claim 26 wherein the process further comprises adding the phase-transfer catalyst to the methylene chloride prior to the step of contacting the methylene chloride with the aqueous phase.

* * * * *

UNITED STATES PATENT AND TRADEMARK OFFICE
CERTIFICATE OF CORRECTION

PATENT NO. : 4,967,021

DATED : October 30, 1990

INVENTOR(S) : Cal Y. Meyers and Roch Chan-Yu-King

It is certified that error appears in the above-identified patent and that said Letters Patent is hereby corrected as shown below: ON TITLE PAGE:

"[75] Inventors: Cal Y. Meyers; Roch Chan-Yu-King, both of Carbondale, Ill." should read ---[75] Inventors: Cal Y. Meyers of Carbondale, Ill.; Roch Chan-Yu-King of Chickasha, Okla.---.

"[73] Assignee: Southern Illinois University Foundation, Carbondale, Ill." should read ---[73] Assignee: Cal Y. Meyers and Roch Chan-Yu-King.---.

Signed and Sealed this

Twenty-first Day of July, 1992

Attest:

DOUGLAS B. COMER

Attesting Officer

Acting Commissioner of Patents and Trademarks